US012702325B2

(12) United States Patent
Eder

(10) Patent No.: US 12,702,325 B2
(45) Date of Patent: Aug. 11, 2026

(54) SKIN FLAP THICKNESS ESTIMATION

(71) Applicant: Cochlear Limited, Macquarie University (AU)

(72) Inventor: Helmut Christian Eder, Bemboka (AU)

(73) Assignee: Cochlear Limited, Macquarie University (AU)

( * ) Notice: Subject to any disclaimer, the term of this patent is extended or adjusted under 35 U.S.C. 154(b) by 486 days.

(21) Appl. No.: 18/248,485

(22) PCT Filed: Sep. 2, 2021

(86) PCT No.: PCT/IB2021/058021
§ 371 (c)(1),
(2) Date: Apr. 10, 2023

(87) PCT Pub. No.: WO2022/079505
PCT Pub. Date: Apr. 21, 2022

(65) Prior Publication Data

US 2023/0389819 A1 Dec. 7, 2023

Related U.S. Application Data

(60) Provisional application No. 63/090,783, filed on Oct. 13, 2020.

(51) Int. Cl.
*A61B 5/107* (2006.01)
*A61N 1/05* (2006.01)

(52) U.S. Cl.
CPC .......... *A61B 5/1075* (2013.01); *A61N 1/0541* (2013.01)

(58) Field of Classification Search
None
See application file for complete search history.

(56) References Cited

U.S. PATENT DOCUMENTS 6,088,619 A 7/2000 Hein et al.
6,212,431 B1 4/2001 Hahn et al.
6,246,911 B1 6/2001 Seligman
6,745,077 B1 6/2004 Griffith et al.
(Continued)

FOREIGN PATENT DOCUMENTS

WO WO-2020131963 A1 * 6/2020 ............. H04R 5/033

OTHER PUBLICATIONS

International Search Report and Written Opinion in counterpart International Application No. PCT/IB2021/058021, mailed Dec. 8, 2021, 7 pages.

*Primary Examiner* — Etsub D Berhanu
(74) *Attorney, Agent, or Firm* — Edell, Shapiro & Finnan, LLC

(57) ABSTRACT

Presented herein are techniques for estimating skin flap thickness ("SFT") of a recipient of an implantable medical device system. In particular, in accordance with the techniques presented herein, the implantable medical device comprises an external component having a magnet configured to magnetically couple the external component to an implantable component of the implantable medical device system through a skin flap of a recipient of the implantable medical device system. The SFT is estimated based on a strength of the magnet. One or more operational parameters for the implantable medical device system may be determined and/or set based on the estimated SFT.

29 Claims, 9 Drawing Sheets

(56) References Cited

U.S. PATENT DOCUMENTS

| | | | | |
|---|---|---|---|---|
| 6,810,289 | B1 | 10/2004 | Shaquer | |
| 7,450,994 | B1 | 11/2008 | Mishra et al. | |
| 7,920,924 | B2 | 4/2011 | Mishra et al. | |
| 8,452,412 | B2 | 5/2013 | Ibrahim | |
| 9,571,166 | B2 | 2/2017 | Metzenthen | |
| 10,080,893 | B2 | 9/2018 | Meskens | |
| 2007/0100395 | A1* | 5/2007 | Ibrahim | A61B 5/4872 607/57 |
| 2009/0030485 | A1* | 1/2009 | Mishra | A61N 1/36038 607/57 |
| 2010/0292759 | A1 | 11/2010 | Hahn et al. | |
| 2013/0221912 | A1* | 8/2013 | Kang | H02J 50/40 320/108 |
| 2014/0277248 | A1* | 9/2014 | Younker | H01M 10/488 607/36 |
| 2015/0119687 | A1 | 4/2015 | Hornsteiner | |
| 2015/0377832 | A1 | 12/2015 | Fung et al. | |
| 2018/0221662 | A1* | 8/2018 | Devcic | G01R 21/133 |
| 2018/0302728 | A1* | 10/2018 | Andersson | H04R 25/606 |
| 2018/0352349 | A1* | 12/2018 | Fung | H04R 25/606 |

* cited by examiner 104
106
150
180
141
IMPLANT
CONFIGURATION
SYSTEM
190
185

102
COCHLEAR IMPLANT 112
IMPLANT BODY 134
139
146
144
116
136
142
STIMULATOR UNIT
143
138
140
RF INTERFACE CIRCUITRY
N
152
114
115 SKIN FLAP
150
108
123
122
RF TRANSCEIVER
RECHARGEABLE BATTERY
124
125
126
128
PROCESSOR(S)
SOUND PROCESSING LOGIC
MEMORY
105
118
119
120
SOUND INPUT DEVICE(S)
AUXILIARY INPUT DEVICE(S)
WIRELESS TRANSCEIVER
EXTERNAL COMPONENT 104
SOUND PROCESSING UNIT 106
121
113
190
185
180
IMPLANT CONFIGURATION SYSTEM

FIG. 5
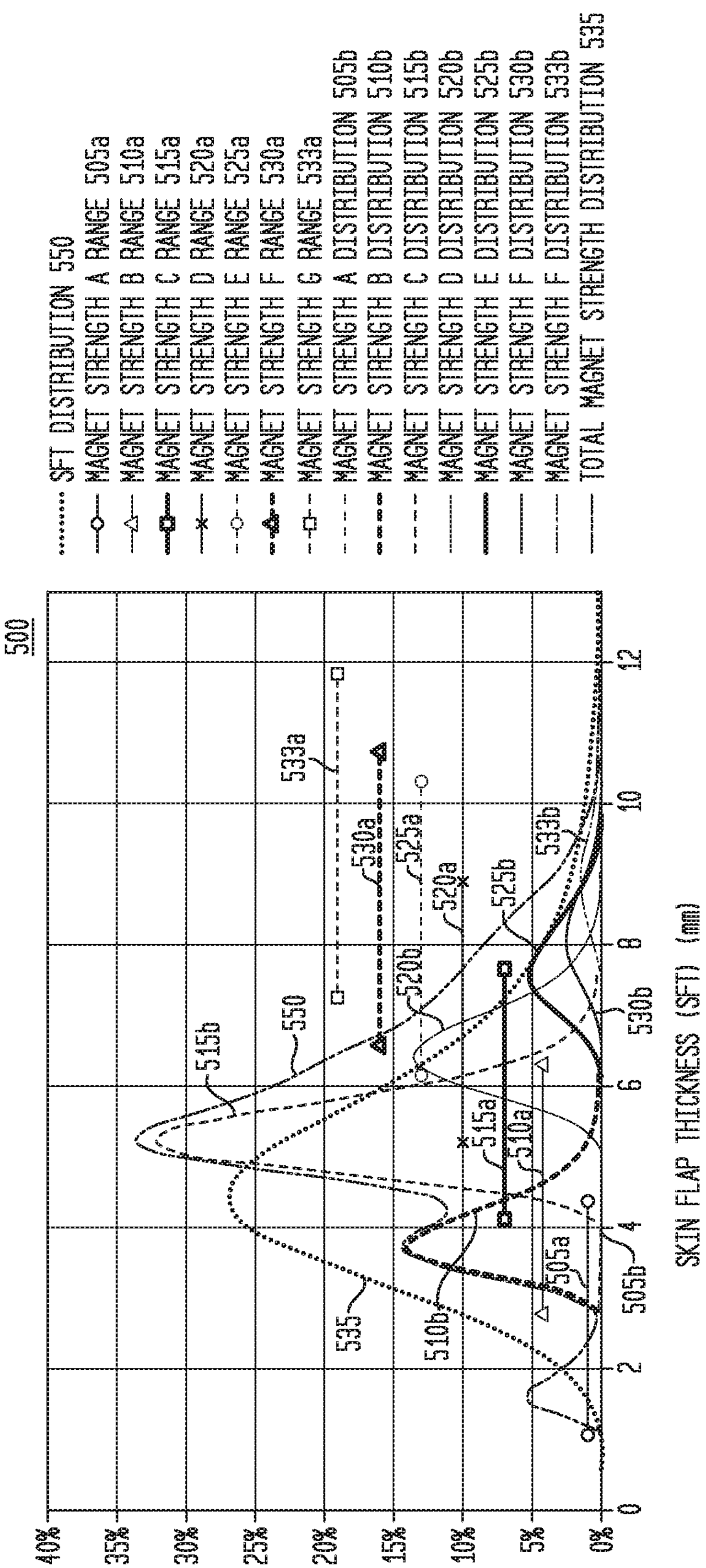

EXTERNAL BATTERY AUTONOMY
900
915
24 HOURS
22 HOURS
20 HOURS
18 HOURS
16 HOURS
14 HOURS
12 HOURS
TIME
905

EXTERNAL BATTERY AUTONOMY
800
810
SFT
10mm
8mm
6mm
4mm
2mm
815
RECIPIENT RANGE
RANGE MOVES DEPENDING ON MAGNET STRENGTH
15 HOURS
18 HOURS
21 HOURS
23 HOURS
19 HOURS
TIME
805

1116
STIMULATING ASSEMBLY
1144(2)
1144(3)
1144(1)
1112
1136
1138
1134
1114
1152
1115
SKIN/TISSUE
1102
VESTIBULAR NERVE STIMULATOR SYSTEM
1105
1150
1108
EXTERNAL DEVICE 1104
1190
1185
1180

SKIN FLAP THICKNESS ESTIMATION

BACKGROUND

Field of the Invention

The present invention relates generally to skin flap thickness estimation for implantable medical devices.

Related Art

Medical devices have provided a wide range of therapeutic benefits to recipients over recent decades. Medical devices can include internal or implantable components/devices, external or wearable components/devices, or combinations thereof (e.g., a device having an external component communicating with an implantable component). Medical devices, such as traditional hearing aids, partially or fully-implantable hearing prostheses (e.g., bone conduction devices, mechanical stimulators, cochlear implants, etc.), pacemakers, defibrillators, functional electrical stimulation devices, and other medical devices, have been successful in performing lifesaving and/or lifestyle enhancement functions and/or recipient monitoring for a number of years.

The types of medical devices and the ranges of functions performed thereby have increased over the years. For example, many medical devices, sometimes referred to as "implantable medical devices," now often include one or more instruments, apparatus, sensors, processors, controllers or other functional mechanical or electrical components that are permanently or temporarily implanted in a recipient. These functional devices are typically used to diagnose, prevent, monitor, treat, or manage a disease/injury or symptom thereof, or to investigate, replace or modify the anatomy or a physiological process. Many of these functional devices utilize power and/or data received from external devices that are part of, or operate in conjunction with, implantable components.

SUMMARY

In one aspect, a method is provided. The method comprises: identifying a strength of a magnet of an external component of an implantable medical device system, the magnet being configured to magnetically couple the external component to an implantable component of the implantable medical device system through a skin flap of a recipient of the implantable medical device system; estimating a thickness of the skin flap based on the strength of the magnet; and determining at least one operational parameter of the implantable medical device system based on the estimated thickness of the skin flap.

In another aspect, a method is provided. The method comprises: providing an external component of an implantable medical device system, wherein the external component comprises a magnet for magnetically coupling the external component to an implantable component through a skin flap of a recipient of the implantable medical device system; and estimating a thickness of the skin flap based on the magnet.

In another aspect, one or more non-transitory computer readable storage media are provided. The non-transitory computer readable storage media comprises instructions that, when executed by at least one processor, are operable to: estimate a thickness of a skin flap through which a magnet of an external component of an implantable medical device system is configured to magnetically couple the external component to an implantable component of the implantable medical device system based on the magnet; and determine at least one operational parameter of the implantable medical device system based on the estimated thickness of the skin flap.

BRIEF DESCRIPTION OF THE DRAWINGS

Embodiments of the present invention are described herein in conjunction with the accompanying drawings, in which:

FIG. 5 is a graph illustrating skin flap thickness ranges and expected use distributions corresponding to different external magnet strengths, in accordance with certain embodiments presented herein;

DETAILED DESCRIPTION

Figures 1, 2:
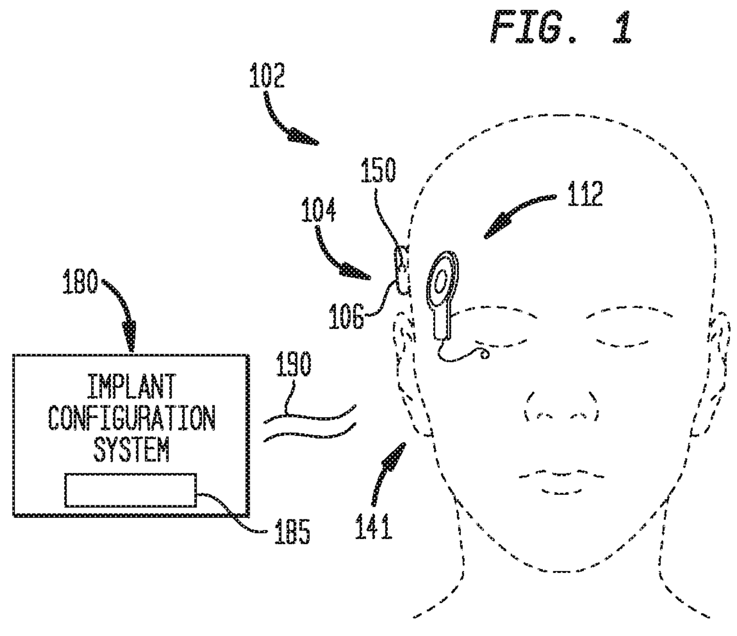
FIG. 1 is a schematic diagram illustrating a cochlear implant system implanted in a head of a recipient and an implant configuration system associated with the cochlear implant system, in accordance with certain embodiments presented herein.
FIG. 2 is a schematic diagram illustrating the cochlear implant system and implant configuration system of FIG. 1, showing a side view of the recipient wearing a sound processing unit of the cochlear implant system, in accordance with certain embodiments presented herein.

Presented herein are techniques for estimating skin flap thickness ("SFT") of a recipient of an implantable medical device system and using the estimated SFT to determine one or more operational parameters of the implantable medical device system. In particular, in accordance with the techniques presented herein, the implantable medical device comprises an external component having a magnet configured to magnetically couple the external component to an implantable component of the implantable medical device system through a skin flap of a recipient of the implantable medical device system. The SFT is estimated based on a strength of the magnet. For example, an SFT or range of SFTs can be estimated using empirical and/or probabilistic distribution data.

One or more operational parameters for the implantable medical device system may be determined based on the estimated SFT. The operational parameters can include any settings or characteristics related to calibrating or using the implantable medical system, such as a battery autonomy and/or a suitability of a battery type for the external component, and/or factors related to signal strength, attenuation, coil tuning, recipient map parameters, etc. For example, the SFT may be estimated, and each operational parameter may be determined and/or set, using one or more lookup tables, charts, or algorithmic models derived from one or more sets of empirical, probabilistic, or other data.

Merely for ease of description, the techniques presented herein are primarily described with reference to a specific implantable medical device system, namely a cochlear implant system. However, it is to be appreciated that the techniques presented herein may also be implemented by other types of implantable medical devices or implantable medical device systems. For example, the techniques presented herein may be implemented by other auditory prosthesis systems that include one or more other types of auditory prostheses, such as middle ear auditory prostheses, bone conduction devices, direct acoustic stimulators, electro-acoustic prostheses, auditory brain stimulators, etc. The techniques presented herein may also be used with tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Example embodiments that may be used to implement the features and functionality of this disclosure will now be described with more particular reference to the accompanying figures in which like reference numerals represent like elements throughout the figures for purposes of simplicity and clarity. Each example embodiment described herein is illustrative and is not to be construed as a preferred or advantageous embodiment, but rather as one example or illustration of a possible embodiment. While reference may be made to the spatial relationships between various components and to the spatial orientation of various aspects of components as depicted in the figures, as will be recognized by those skilled in the art after a complete reading of the present disclosure, the devices, components, members, apparatuses, etc. described herein may be positioned in any desired orientation.

When used to describe a range of dimensions and/or other characteristics (e.g., time, distance, length, etc.) of an element, operations, conditions, etc. the phrase "between X and Y" represents a range that includes X and Y. Similarly, when used herein, the term "approximately" and terms of its family (such as "approximate", etc.) should be understood as indicating values very near to those which accompany the aforementioned term. That is to say, a deviation within reasonable limits from an exact value should be accepted, because a skilled person in the art will understand that such a deviation from the values indicated is inevitable due to measurement inaccuracies, etc. The same applies to the terms "about" and "around" and "substantially". Similarly, when used herein, the term "comprises" and its derivations (such as "comprising", etc.) should not be understood in an excluding sense, that is, these terms should not be interpreted as excluding the possibility that what is described and defined may include further elements, steps, etc.

Referring initially to FIGS. 1-4, which are generally described together for ease of description, an example cochlear implant system 102 can be implanted in a head 141 of a person, animal, or other recipient (each referred to herein as a "recipient"). The cochlear implant system 102 includes an external component 104 and an implantable component 112. The implantable component 112 is sometimes referred to as a "cochlear implant."

Figure 3:
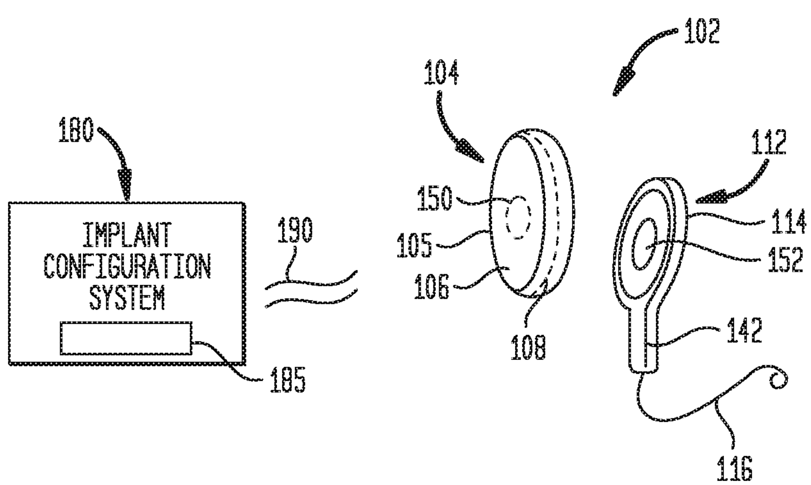
FIG. 3 is a schematic diagram illustrating the cochlear implant system and implant configuration system of FIG. 1, showing components of the cochlear implant system without the recipient's head for purposes of clarity, in accordance with certain embodiments presented herein.
Figure 4:
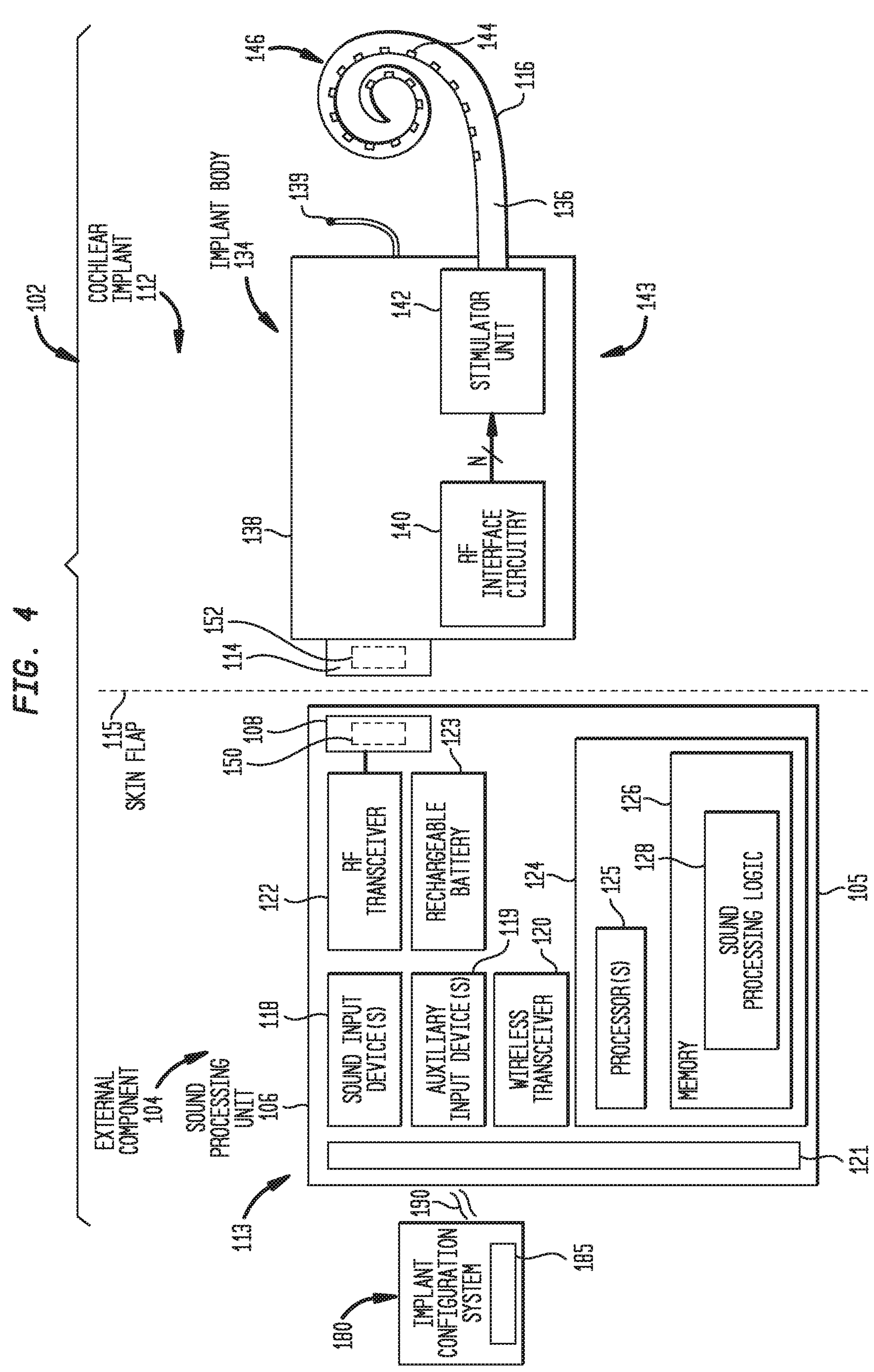
FIG. 4 is a block diagram of the cochlear implant system and implant configuration system of FIG. 1, in accordance with certain embodiments presented herein.

FIG. 1 is a schematic diagram illustrating the implantable component 112 implanted in the head 141 of the recipient, while FIG. 2 is a schematic diagram illustrating the external component 104 worn on the head 141 of the recipient. As described in more detail below, the external component 104 and implantable component 112 are generally configured to cooperate to mimic the function of a healthy inner ear (or cochlea), e.g., to help provide the recipient clearer sound than what they would hear without the cochlear implant system 102. FIG. 3 includes another schematic view of the cochlear implant system 102, including both the external component 104 and the implantable component 112, but without the recipient's head being shown for purposes of clarity. FIG. 4 is a block diagram illustrating further details of the cochlear implant system 102 and an implant configuration system 180 associated with the cochlear implant system 102, in accordance with certain embodiments presented herein.

As noted, the cochlear implant system 102 includes an external component 104 that is configured to be directly or indirectly attached to the body of the recipient and an implantable component 112 configured to be implanted in the recipient. In the examples of FIGS. 1-4, the external component 104 comprises a sound processing unit 106, which is an off-the-ear (OTE) sound processing unit sometimes referred to as an "OTE component." The sound processing unit 106 is configured to send data and power to the implantable component 112 as described below.

In general, the sound processing unit 106 includes a generally cylindrically shaped housing 105, which is configured to be magnetically coupled to the recipient's head 141. For example, the sound processing unit 106 can include an integrated external magnet 150 configured to be magnetically coupled to an implantable magnet 152 in the implantable component 112. The sound processing unit 106 also includes an integrated external coil 108 that is configured to be wirelessly (e.g., inductively) coupled to an implantable coil 114 of the implantable component 112 as described below. In FIGS. 1-3, the external magnet 150 is shown using dashed lines, indicating it is integrated within the housing 105 of the sound processing unit 106. In FIG. 4, the external magnet 150 and the implantable magnet 152 are shown using dashed lines, indicating the external coil 108 and the implantable coil 114 are disposed around the magnet 150 and magnet 152, respectively.

It is to be appreciated that the OTE sound processing unit 106 is merely illustrative of the external devices that could operate with the implantable component 112. For example, in alternative examples, the external component may comprise a behind-the-ear (BTE) sound processing unit or a micro-BTE sound processing unit and a separate external coil assembly. In general, a BTE sound processing unit comprises a housing that is shaped to be worn on the outer ear of the recipient and is connected to the separate external coil assembly via a cable, where the external coil assembly is configured to be magnetically and inductively coupled to the implantable coil 114. It is also to be appreciated that alternative external components could be located in the recipient's ear canal, worn on the body, etc.

While FIGS. 1-4 illustrate an arrangement in which the cochlear implant system 102 includes an external component, it is to be appreciated that embodiments of the present invention may be implemented in cochlear implant systems having alternative arrangements. For example, embodiments presented herein can be implemented by a totally implantable cochlear implant or other totally implantable medical device. A totally implantable medical device is a device in which all components of the device are configured to be implanted under skin/tissue of a recipient. Because all components are implantable, a totally implantable medical device operates, for at least a finite period of time, without the need of an external device/component. However, an external component can be used to, for example, charge the internal power source (battery) of the totally implantable medical device.

Returning to the specific example of FIGS. 1-4, FIG. 4 illustrates that the sound processing unit 106 comprises one or more input devices 113 that are configured to receive input signals (e.g., sound or data signals). The one or more input devices 113 include one or more sound input devices 118 (e.g., microphones, audio input ports, telecoils, etc.), one or more auxiliary input devices 119 (e.g., audio ports, such as a Direct Audio Input (DAI), data ports, such as a Universal Serial Bus (USB) port, cable port, etc.), and a wireless transmitter/receiver (transceiver) 120. However, it is to be appreciated that the one or more input devices 113 may include additional types of input devices and/or less input devices (e.g., the wireless transceiver 120 and/or one or more auxiliary input devices 119 could be omitted).

The sound processing unit 106 also comprises the external coil 108, a charging coil 121, a closely-coupled transmitter/receiver (transceiver) 122, sometimes referred to as a radiofrequency (RF) transceiver 122, at least one rechargeable battery 123, and a processing module 124. The processing module 124 comprises one or more processors 125 and a memory device (memory) 126 that includes sound processing logic 128. The memory device 126 may comprise any one or more of: Non-Volatile Memory (NVM), Ferroelectric Random Access Memory (FRAM), read only memory (ROM), random access memory (RAM), magnetic disk storage media devices, optical storage media devices, flash memory devices, electrical, optical, or other physical/tangible memory storage devices. The one or more processors 125 are, for example, microprocessors or microcontrollers that execute instructions for the sound processing logic 128 stored in memory device 126.

The implantable component 112 comprises an implant body (main module) 134, a lead region 136, and an intra-cochlear stimulating assembly 116, all configured to be implanted under a skin flap 115 of the recipient. The skin flap 115 includes skin, flesh, and other tissue that is generally disposed between the external component 104 and the implantable component 112, e.g., in the head 141 of the recipient. The magnets 150 and 152 magnetically couple the external component 104 to the implantable component 112 through the skin flap 115 as described below. The implant body 134 generally comprises a hermetically-sealed housing 138 in which RF interface circuitry 140 and a stimulator unit 142 are disposed. The implant body 134 also includes the internal/implantable coil 114 that is generally external to the housing 138, but which is connected to the transceiver 140 via a hermetic feedthrough (not shown in FIG. 4).

The stimulating assembly 116 is configured to be at least partially implanted in the recipient's cochlea. The stimulating assembly 116 includes a plurality of longitudinally spaced intra-cochlear electrical stimulating contacts (electrodes) 144 that collectively form a contact or electrode array 146 for delivery of electrical stimulation (current) to the recipient's cochlea. The stimulating assembly 116 extends through an opening in the recipient's cochlea (e.g., cochleostomy, the round window, etc.) and has a proximal end connected to stimulator unit 142 via the lead region 136 and hermetic feedthrough. The lead region 136 includes a plurality of conductors (wires) that electrically couple the electrodes 144 to the stimulator unit 142. The implantable component 112 also includes an electrode outside of the cochlea, sometimes referred to as the extra-cochlear electrode (ECE) 139.

As noted, the cochlear implant system 102 includes the external coil 108 and the implantable coil 114. In certain example embodiments, the external magnet 150 is fixed relative to the external coil 108, and the implantable magnet 152 is fixed relative to the implantable coil 114. The magnets 150 and 152 can facilitate operational alignment of the external coil 108 with the implantable coil 114 thereby enabling the external component 104 to transmit data and power to the implantable component 112 via a closely-coupled wireless link formed between the coils 108 and 114. In certain examples, the closely-coupled wireless link is a radio frequency (RF) link. However, various other types of energy transfer, such as infrared (IR), electromagnetic, capacitive and inductive transfer, may be used to transfer the power and/or data from an external component to an implantable component and, as such, FIGS. 1-4 illustrate only one example arrangement. For example, the external coil 108 can be in electrical communication with a power supply (e.g., the rechargeable battery 123) and can induce a current in the implantable coil 114, via an inductive link between the coils 108 and 114, to supply power to the implantable component 112.

Performance of the wireless link between the coils 108 and 114 can impact operational characteristics of the cochlear implant system 102, such as power consumption, capacity, and efficiency, signal strength, signal/audio attenuation, signal-to-noise ratios, etc. A thickness of the skin flap 115 between the coils 108 and 114 can be an important factor in the performance of the wireless link. For example, a thicker skin flap 115 may correspond to a further separation distance between the coils 108 and 114 and, therefore, a weaker wireless link between the coils 108 and 114. Similarly, a thinner skin flap 115 may correspond to a shorter separation distance between the coils 108 and 114 and, therefore, a stronger wireless link between the coils 108 and 114.

The thickness of the skin flap 115 typically is established during a surgery in which the implantable component 112 is implanted within the recipient's body. For example, the surgeon can arrange the skin flap 115 to be thick enough to provide structural integrity for the cochlear implant system 102 yet not so thick that it impedes the wireless link between the coils 108 and 114. For example, the thickness of the skin flap 115 may be between about 0 mm and about mm, though the thickness may be larger than 10 mm.

After the implantable component 112 is placed within the recipient's head 141, the external component 104 is attached to the head 141, with the external magnet 150 of the external component 104 magnetically coupling the external component 104 to the implantable magnet 152 of the implantable component 112 through the skin flap 115. While a strength of the implantable magnet 152 generally is fixed and cannot readily be changed post-surgery, a strength of the external magnet 150 may be customized for the recipient. For example, different external components 104 with different external magnets 150 having different strengths may be selectively coupled and decoupled to the implantable component 112 until the external component 104 with the most suitable external magnet 150 is chosen. Alternatively, the external magnet 150 may be removably integrated within the housing 105, and different external magnets 150 having different strengths may be integrated and de-integrated within the housing 105 until the most suitable external magnet 150 is chosen.

The external magnet 150 may be chosen to provide as comfortable of a fit as possible for the recipient while achieving an appropriate strength of attraction between the external magnet 150 and the implantable magnet 152. While a stronger external magnet 150 may provide a stronger coupling with the implantable magnet 152, e.g., making it less likely for the external magnet 150 to fall off during use, the stronger external magnet 150 could cause pain for the recipient, e.g., by pulling on the recipient's head or creating a rash on the recipient's skin. The strength of the external magnet 150 may be selected to balance these concerns. For example, the external magnet 150 could be selected from magnets having strengths of about ½M (weakest, e.g., 0.150 kGauss), 1 M (e.g., 0.245 kGauss), 2 M (e.g., 0.355 kGauss), 3 M (e.g., 0.460 kGauss), 4 M (e.g., 0.600 kGauss), 5 M (e.g., 0.690 kGauss), or 6 M (strongest, e.g., 0.820 kGauss). As would be recognized by a person of ordinary skill in the art, this range of magnet strengths is illustrative and should not be construed as being limiting in any way.

As noted above, the sound processing unit 106 includes the processing module 124. The processing module 124 is configured to convert received input signals (received at one or more of the input devices 113) into output signals for stimulating a first ear of a recipient (i.e., the processing module 124 is configured to perform sound processing on input signals received at the sound processing unit 106). Stated differently, the one or more processors 125 are configured to execute hybrid multi-phasic processing logic 128 in memory 126 to convert the received input signals into output signals that represent electrical stimulation for delivery to the recipient. Electrical stimulation signals in accordance with embodiments presented can comprise hybrid multi-phasic stimulation signals. As such, the output signals generated by the sound processing unit 106 represent the hybrid multi-phasic stimulation signals (e.g., comprise commands/data for use by the stimulator unit 142 to form hybrid multi-phasic stimulation signals).

As noted, FIG. 4 illustrates an embodiment in which the processing module 124 in the sound processing unit 106 generates the output signals. In an alternative embodiment, the sound processing unit 106 can send less processed information (e.g., audio data) to the implantable component 112 and the sound processing operations (e.g., conversion of sounds to output signals) can be performed by a processor within the implantable component 112. That is, the implantable component 112, rather than the sound processing unit 106, could include a processing module that is similar to processing module 124 of FIG. 4.

Returning to the specific example of FIG. 4, the output signals are provided to the RF transceiver 122, which transcutaneously transfers the output signals (e.g., in an encoded manner) to the implantable component 112 via the external coil 108 and the implantable coil 114. That is, the output signals are received at the RF interface circuitry 140 via the implantable coil 114 and provided to the stimulator unit 142. The stimulator unit 142 is configured to utilize the output signals to generate electrical stimulation signals (e.g., current signals) for delivery to the recipient's cochlea via "stimulation channels," where each stimulating channel comprises one or more of the stimulating contacts 144. In this way, the cochlear implant system 102 electrically stimulates the recipient's auditory nerve cells, bypassing absent or defective hair cells that normally transduce acoustic vibrations into neural activity, in a manner that causes the recipient to perceive one or more components of the received sound signals.

The implant configuration system 180 includes a memory and processor with logic 185 for determining and/or setting operational parameters for the cochlear implant system 102. The operational parameters can include any settings or characteristics related to calibrating or using the cochlear implant system 102. For example, the operational parameters can include a battery autonomy or battery type suitability for the external component 104, factors related to signal strength and/or attenuation (e.g., for the wireless link and/or for audio microphones of the cochlear implant system 102), coil tuning, recipient map parameters (e.g., minimum auditory detection sound thresholds, maximum sound stimulation comfort levels, and channel rates), etc.

In certain example embodiments, the implant configuration system 180 is configured to determine and/or set the operational parameters based on the strength of the external magnet 150. For example, as described in more detail below, the implant configuration system 180 can be configured to estimate the thickness of the skin flap 115 based on the strength of the external magnet 150 and to determine the operational parameters based on the estimated skin flap thickness (SFT). The implant configuration system 180 can provide and/or display the determined operational parameters (e.g., to the recipient and/or a clinician aiding the recipient) and/or adjust one or more settings associated with the cochlear implant system 102 based on the determined operational parameters via one or more data links 190, such as a wired connection, a wireless network, radio frequency, infrared, or another suitable wired or wireless communication mechanism or combinations thereof.

FIG. 5 is a graph 500 illustrating SFT ranges and expected use distributions corresponding to different external magnet strengths, in accordance with certain embodiments presented herein. As illustrated in the graph 500, each external magnet strength is generally associated with a corresponding range of SFTs. For example, a weaker magnet may generally be suitable for use with recipients having thinner skin flaps, while a stronger magnet may generally be required for use with recipients having thicker skin flaps.

In the graph 500, an example magnet having a strength A, e.g., a strength of ½M, may correspond to an SFT range 505*a* of about 1.1 mm to about 4.4 mm; an example magnet having a strength B, e.g., a strength of 1 M, may correspond to an SFT range 510*a* of about 2.8 mm to about 6.4 mm; an example magnet having a strength C, e.g., a strength of 2 M, may correspond to an SFT range 515*a* of about 4.1 mm to about 7.7 mm; an example magnet having a strength D, e.g., a strength of 3 M, may correspond to an SFT range 520*a* of about 5.1 mm to about 9.0 mm; a magnet having a strength E, e.g., a strength of 4 M, may correspond to an SFT range 525*a* of about 6.2 mm to about 10.3 mm; a magnet having a strength F, e.g., a strength of 5 M, may correspond to an SFT range 530*a* of about 6.6 mm to about 10.8 mm; and a magnet having a strength G, e.g., a strength of 6 M, may correspond to an SFT range 533*a* of about 7.3 mm to about 11.9 mm. As would be recognized by a person of ordinary skill in the art, the SFT ranges are illustrative and should not be construed as being limiting in any way.

As further illustrated in the graph 500, each example magnet strength generally corresponds to an expected use distribution relative to SFT. For example, while the SFT range 520*a* for the example magnet having the strength D extends between about 5.1 mm and 9.0 mm, the expected SFT for a set of recipients wearing that magnet is weighted along a distribution curve 520*b*, which is biased to the lower end of the range 520*a*. Thus, for example, it would be more likely for a recipient wearing a magnet having the strength D to have an SFT between about 5.1 mm and about 7.0 mm than it would be for the recipient to have an SFT between about 7.0 mm and 9.0 mm, even though the middle of the range 520*a* is approximately 7.1 mm. Similarly, the SFT range 505*a* for the example magnet having the strength A may have an expected use distribution 505*b* relative to SFT; the SFT range 510*a* for the example magnet having the strength B may have an expected use distribution 510*b* relative to SFT; the SFT range 515*a* for the example magnet having the strength C may have an expected distribution 515*b* relative to SFT; the SFT range 525*a* for example magnet having the strength E may have an expected distribution 525*b* relative to SFT; the SFT range 530*a* for the example magnet having the strength F may have an expected distribution 530*b* relative to SFT; and the SFT range 533*a* for the example magnet having the strength G may have an expected distribution 533*b* relative to SFT.

The expected use distributions may be determined, e.g., based on empirical clinical data and/or probabilistic data. For example, the expected use distributions may be calculated based on actual uses or expected uses of magnets for a set of patients having known SFTs. A total SFT distribution 550, which shows an expected total distribution of SFTs for a set of recipients, may generally align with a total of the expected use distributions 535. As would be recognized by a person of ordinary skill in the art, the distributions and totals in the graph 500 are illustrative and should not be construed as being limiting in any way.

As described in more detail below, in certain example embodiments, a recipient's SFT may be estimated based on a known magnet strength in accordance with the principles in the graph 500. For example, if it is known that a cochlear implant system for a particular recipient includes an external magnet with a strength D, an SFT for the recipient may be estimated to be between about 5.1 mm and 9.0 mm, with an expected range of the SFT between about 5.1 mm and 7.0 mm. The estimated SFT may include a range of SFT values or a single SFT measurement within the range. For example, the single SFT measurement may be selected based on the magnet strength and certain other recipient and/or implant data relevant to SFT, such as an age of the recipient. The estimated SFT may be used, for example, to determine and/or set one or more operational parameters for the cochlear implant system as described below.

Figure 6:
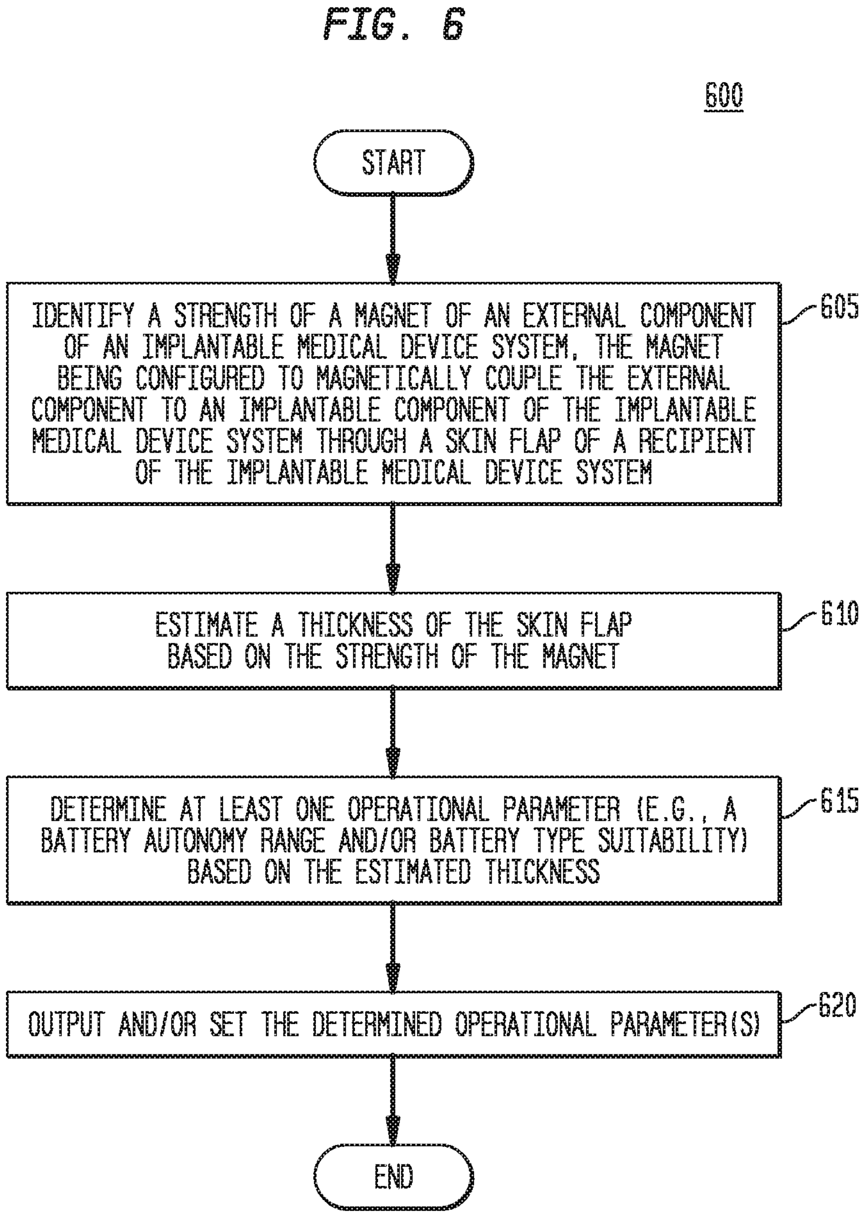
FIG. 6 is a flow chart of a method for determining operational parameters of an implantable medical device system, in accordance with certain embodiments presented herein.

FIG. 6 is a flow chart of a method 600 for determining operational parameters of an implantable medical device system, in accordance with certain embodiments presented herein. For example, the method 600 may be implemented by an implant configuration system, such as the implant configuration system 180 described above with reference to FIGS. 1-4. The method 600 begins in step 605 in which a strength of a magnet of an external component of an implantable medical device system is identified. The magnet is configured to magnetically couple the external component to an implantable component of the implantable medical device system through a skin flap of a recipient of the implantable medical device system. For example, the implantable medical device system can be a cochlear implant system, and the magnet can be an external magnet of the cochlear implant system. The magnet can have any strength. For example, the magnet could have a strength between about ½M (weakest) and about 6 M (strongest), though the strength could be below ½M and above 6 M.

In step 610, a thickness of the skin flap is estimated based on the strength of the magnet. For example, as described above in connection with FIG. 5, an SFT or range of SFTs can be estimated based on the strength of the magnet, e.g., using empirical and/or probabilistic distribution data. Estimation may involve, for example, mapping the strength of the magnet to the SFT or range of SFTs using one or more lookup tables or charts or inputting the magnet strength into an algorithmic model derived from one or more sets of empirical, probabilistic, or other data.

In certain example embodiments, the estimation in step 610 may be performed in lieu of, or in addition to, using direct RF link characterizations or other measurements to determine SFT. For example, estimation using magnet strength may be performed by or for a recipient without the need for a clinical visit. However, for data validation or other purposes, the estimation could (but does not necessarily have to) be compared or confirmed with an SFT value calculated through other, clinical means.

In step 615, at least one operational parameter of the implantable medical system is determined based on the estimated SFT. The operational parameter(s) can include any settings or characteristics related to calibrating or using the implantable medical system. For example, with respect to a cochlear implant system, the operational parameters can include a battery autonomy or battery type suitability for the external component, factors related to signal strength and/or attenuation (e.g., for a wireless link and/or for audio microphones of the cochlear implant system), coil tuning, recipient map parameters (e.g., minimum auditory detection sound thresholds, maximum sound stimulation comfort levels, and channel rates), etc. Each operational parameter may be determined and/or set, e.g., by mapping the estimated SFT to a set of potential operational parameters using one or more lookup tables or charts or inputting the estimated SFT into an algorithmic model derived from one or more sets of empirical, probabilistic, or other data.

For example, the estimated SFT may be included as a "known" value in a signal attenuation algorithm such as $E(x)=E_0e^{-x/\delta}$, where δ is the estimated SFT, a power attenuation algorithm such as $P(x)=P_0e^{-2x/\delta}$, where δ is the estimated SFT, or as an input in other algorithms and/or lookup tables for calculating parameters related to the implantable medical system, such as magnetic field values, sound attenuation, etc.

For example, as described in more detail below with reference to FIGS. 8 and 9, a range of battery autonomy times may be determined in step 615 based on an estimated SFT range. Battery autonomy times may be determined, for example, by using empirical or probabilistic power, voltage, and/or current data to calculate an estimated total current requirement for the implantable medical system. For example, a range of battery autonomy times around 24 hours may be determined for a device that requires a total current of 7.5 mA.

Similarly, a battery type suitability for the external component may be determined based on the estimated SFT range. As would be appreciated by a person of ordinary skill in the art, various different battery types, such as zinc air batteries, lithium ion batteries, and silver oxide batteries, may be used in implantable medical device systems. Suitability of each battery type may vary depending on SFT. For example, zinc air batteries are generally current limited and certain zinc air batteries may not be suitable for recipients with particular SFTs. For example, a battery with a lower current capacity may not be suitable for a particular recipient with a larger SFT.

In step 620, the determined operational parameter(s) are output and/or set. For example, an implant configuration system can provide and/or display the determined operational parameter(s) (e.g., to the recipient and/or a clinician aiding the recipient) via a display of a computing device. In addition, or in the alternative, the implant configuration system can adjust one or more settings based on the determined operational parameter(s) via one or more data links, such as a wired connection, a wireless network, radio frequency, infrared, or another suitable wired or wireless communication mechanism or combinations thereof. The determined operational parameter(s) can be output and/or set by or for the recipient without the need for a clinical visit. However, for data validation or other purposes, the determinations and settings could (but do not necessarily have to) be compared or confirmed with parameter values calculated through other, clinical means.

As would be recognized by a person of skill in the art, the steps associated with the methods of the present disclosure, including method 600, may vary widely. Steps may be added, removed, altered, combined, and reordered without departing from the spirit or the scope of the present disclosure. Therefore, the example methods are to be considered illustrative and not restrictive, and the examples are not to be limited to the details given herein but may be modified within the scope of the appended claims.

Figure 7:
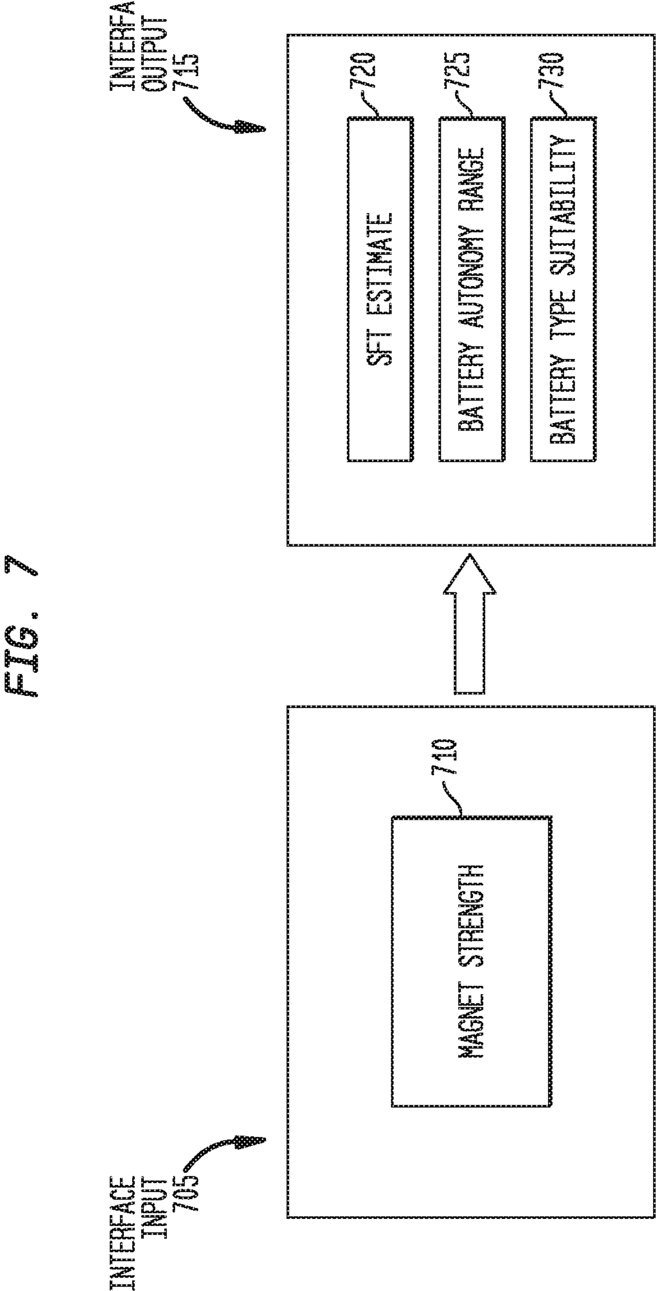
FIG. 7 is a diagram illustrating an example graphical display from an interface input of an implant configuration system and an example graphical display from an interface output of the implant configuration system, in accordance with certain embodiments presented herein.

FIG. 7 illustrates an example graphical display from an interface input 705 of an implant configuration system and an example graphical display from an interface output 715 of the implant configuration system, in accordance with certain embodiments presented herein. As noted above, an implant configuration system can be configured to determine and/or set one or more operational parameters for an implantable medical device system, such as a cochlear implant system. For example, the implant configuration system can display or cause to be displayed one or more interfaces through which a user, such as a recipient of the implantable medical device system or a clinician aiding the recipient of the implantable medical device system, can input and retrieve information regarding the implantable medical device system.

In the example embodiment of FIG. 7, the implant configuration system displays (or causes to be displayed) the interface input 705 through which the user can enter a magnet strength via a field 710. For example, the user could enter the magnet strength by typing a value of the magnet strength into a text field or by selecting a magnet strength from a prepopulated list of potential magnet strengths. Alternatively, the user could simply enter or select a model number, SKU, or other identifier for their magnet or device so that the implant configuration system can determine a corresponding magnet strength for the magnet/device.

The implant configuration system is configured to determine and/or set one or more operational parameters for the implantable medical device system based on the magnet strength. For example, as illustrated in FIG. 7, the implant configuration system can determine, and output via the interface output 715, an SFT estimate 720, a battery autonomy range 725, and a battery type suitability 730 that each correspond to the magnet strength. As would be appreciated, the interface input 705 and interface output 715 depicted in FIG. 7 are illustrative and many suitable variations would be apparent to a person of ordinary skill in the art. In particular, additional, less, or different fields may be included, and the sizes, shapes, and other characteristics of the fields may be different, in alternative example embodiments. For example, fields related to operational parameters other than battery autonomy and battery type suitability may be displayed, including, e.g., fields related to signal strength and/or attenuation, coil tuning, recipient map parameters, etc.

Figure 8:
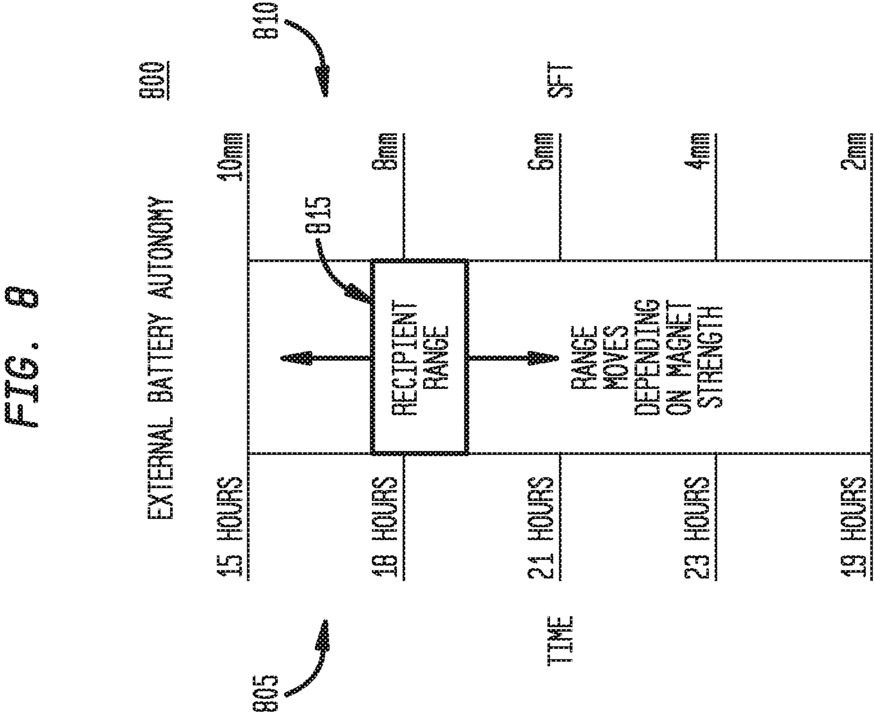
FIG. 8 is a graph illustrating external battery autonomy ranges associated with different skin flap thicknesses, in accordance with certain embodiments presented herein.

FIG. 8 is a graph 800 illustrating external battery autonomy ranges associated with different SFTs, in accordance with certain embodiments presented herein. For example, the graph 800 could be displayed as part of an interface output of an implant configuration system. Alternatively, information based on the graph 800, or principles embodied within the graph 800, could be displayed or used by the implant configuration system without the graph 800 being displayed.

As noted above, an estimated SFT may be used to determine at least one operational parameter of an implantable medical system, including a battery autonomy for an external component of the implantable medical system. For example, for a cochlear implant system, an estimated SFT may be used to determine a battery autonomy for a rechargeable battery of an external component of the cochlear implant system. The estimated SFT may be determined, for example, based on a strength of a magnet of the external component, as described above.

As shown in FIG. 8, an estimated recipient range 815 for SFT and battery autonomy values may be determined on a sliding scale relative to an expected range of SFTs 810 and battery autonomy values 805. For example, a recipient with an estimated SFT between about 7.0 mm and about 8.5 mm may have an expected battery autonomy between about 17 hours and about 19.5 hours. It should be appreciated that a wider range of potential SFT values for the recipient may generally correspond to a wider range of potential battery autonomy values, and a narrower range of potential SFT values for the recipient may correspond to a narrower range of potential battery autonomy values. For example, a singular SFT value may potentially map to a single battery autonomy value, while a range of SFT values may potentially map to a range of battery autonomy values. As would be recognized by a person of ordinary skill in the art, the configuration of the graph 800 and the SFT values, battery autonomy values, and ranges reflected therein are illustrative and should not be construed as being limiting in any way.

Figure 9:
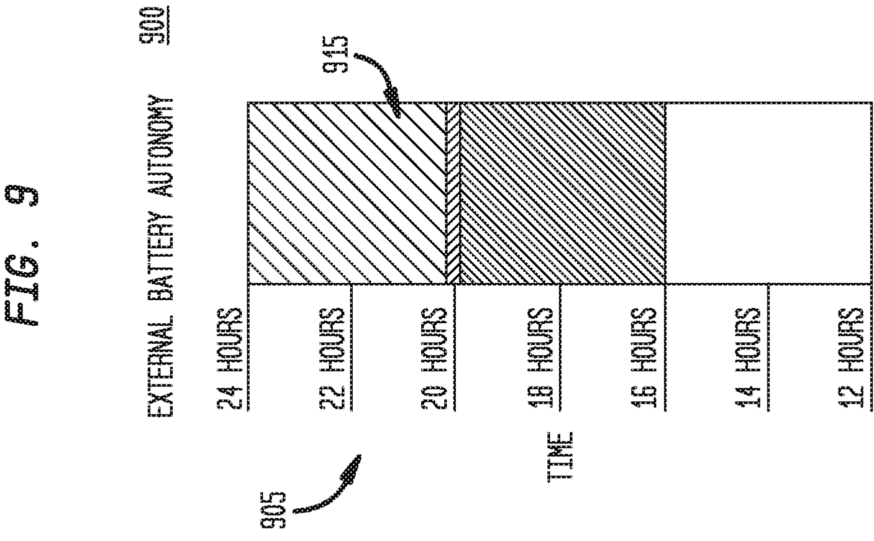
FIG. 9 is a graph illustrating external battery autonomy ranges associated with different skin flap thicknesses, in accordance with certain embodiments presented herein.

FIG. 9 is another graph 900 illustrating external battery autonomy ranges associated with different SFTs, in accordance with certain embodiments presented herein. For example, the graph 900 could be displayed as part of an interface output of an implant configuration system. Alternatively, information based on the graph 900, or principles embodied within the graph 900, could be displayed or used by the implant configuration system without the graph 900 being displayed.

As with the graph 800 described above with reference to FIG. 8, the graph 900 displays an estimated recipient range 915 for battery autonomy values, which may be determined on a sliding scale relative to an expected range of SFTs (not shown) and battery autonomy values 905. In the example embodiment depicted in FIG. 9, the values 905 and range 915 are determined based on the SFT values, though the SFT values may be omitted from display in the graph 900 for user interface design or other reasons. As would be recognized by a person of ordinary skill in the art, the configuration of the graph 900 and the battery autonomy values and ranges reflected therein are illustrative and should not be construed as being limiting in any way.

Figure 10:
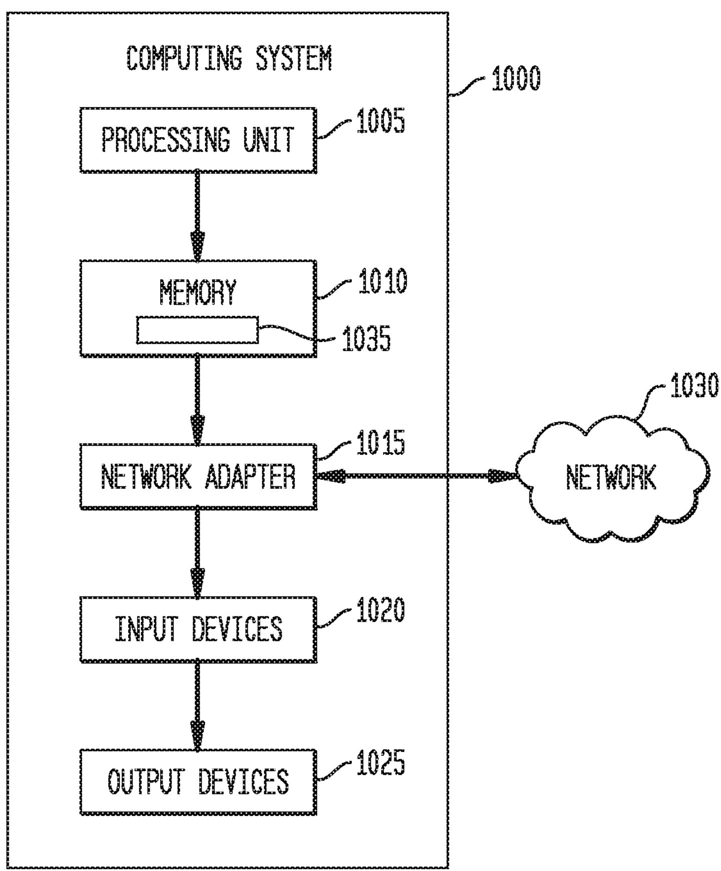
FIG. 10 is a block diagram illustrating a computing device/system configured to implement certain embodiments presented herein.

FIG. 10 illustrates an example of a suitable computing system 1000 with which one or more of the disclosed examples can be implemented. Computing systems, environments, or configurations that can be suitable for use with examples described herein include, but are not limited to, personal computers, server computers, hand-held devices, laptop devices, multiprocessor systems, microprocessor-based systems, programmable consumer electronics (e.g., smart phones), network PCs, minicomputers, mainframe computers, tablets, distributed computing environments that include any of the above systems or devices, and the like. The computing system 1000 can be a single virtual or physical device operating in a networked environment over communication links to one or more remote devices. The remote device can be an auditory prosthesis (e.g., an auditory prosthesis), a personal computer, a server, a router, a network personal computer, a peer device or other common network node.

In its most basic configuration, computing system 1000 includes at least one processing unit 1005 and memory 1010. The processing unit 1005 includes one or more hardware or software processors (e.g., Central Processing Units) that can obtain and execute instructions. The processing unit 1005 can communicate with and control the performance of other components of the computing system 1000.

The memory 1010 is one or more software or hardware-based computer-readable storage media operable to store information accessible by the processing unit 1005. The memory 1010 can store, among other things, instructions executable by the processing unit 1005 to implement applications or cause performance of operations described herein, as well as other data. The memory 1010 can be volatile memory (e.g., RAM), non-volatile memory (e.g., ROM), or combinations thereof. The memory 1010 can include transitory memory or non-transitory memory. The memory 1010 can also include one or more removable or non-removable storage devices. In examples, the memory 1010 can include RAM, ROM, EEPROM (Electronically-Erasable Programmable Read-Only Memory), flash memory, optical disc storage, magnetic storage, solid state storage, or any other memory media usable to store information for later access. In examples, the memory 1010 encompasses a modulated data signal (e.g., a signal that has one or more of its characteristics set or changed in such a manner as to encode information in the signal), such as a carrier wave or other transport mechanism and includes any information delivery media. By way of example, and not limitation, the memory 1010 can include wired media such as a wired network or direct-wired connection, and wireless media such as acoustic, RF, infrared and other wireless media or combinations thereof. In certain embodiments, the memory 1010 comprises implant configuration system logic 1035 that, when executed, enables the processing unit 1005 to perform aspects of the techniques presented.

In the illustrated example, the system 1000 further includes a network adapter 1015, one or more input devices 1020, and one or more output devices 1025. The system 1000 can include other components, such as a system bus, component interfaces, a graphics system, a power source (e.g., a battery), among other components.

The network adapter 1015 is a component of the computing system 1000 that provides network access (e.g., access to at least one network 1030). The network adapter 1015 can provide wired or wireless network access and can support one or more of a variety of communication technologies and protocols, such as ETHERNET, cellular, BLUETOOTH, near-field communication, and RF (Radiofrequency), among others. The network adapter 1015 can include one or more antennas and associated components configured for wireless communication according to one or more wireless communication technologies and protocols.

The one or more input devices 1020 are devices over which the computing system 1000 receives input from a user. The one or more input devices 1020 can include physically-actuatable user-interface elements (e.g., buttons, switches, or dials), touch screens, keyboards, mice, pens, and voice input devices, among others input devices.

The one or more output devices 1025 are devices by which the computing system 1000 is able to provide output to a user. The output devices 1025 can include, displays, speakers, and printers, among other output devices.

It is to be appreciated that the arrangement for computing system 1000 shown in FIG. 10 is merely illustrative and that aspects of the techniques presented herein may be implemented at a number of different types of systems/devices. For example, the computing system 1000 could be a laptop computer, tablet computer, mobile phone, surgical system, etc.

Embodiments presented herein have been primarily described with reference to an example auditory prosthesis system, namely a cochlear implant system. However, as noted above, it is to be appreciated that the techniques presented herein may be implemented by a variety of other types of implantable medical devices (or systems that include other types of implantable medical devices) that provide a wide range of therapeutic benefits to recipients, patients, or other users. For example, the techniques presented herein may be implemented by other auditory prostheses, such as acoustic hearing aids, middle ear auditory prostheses, bone conduction devices, direct acoustic stimulators, electro-acoustic prostheses, other electrically simulating auditory prostheses (e.g., auditory brain stimulators), etc. The techniques presented herein may also be implemented by tinnitus therapy devices, vestibular devices (e.g., vestibular implants), visual devices (i.e., bionic eyes), sensors, pacemakers, drug delivery systems, defibrillators, functional electrical stimulation devices, catheters, seizure devices (e.g., devices for monitoring and/or treating epileptic events), sleep apnea devices, electroporation devices, etc.

Figure 11:
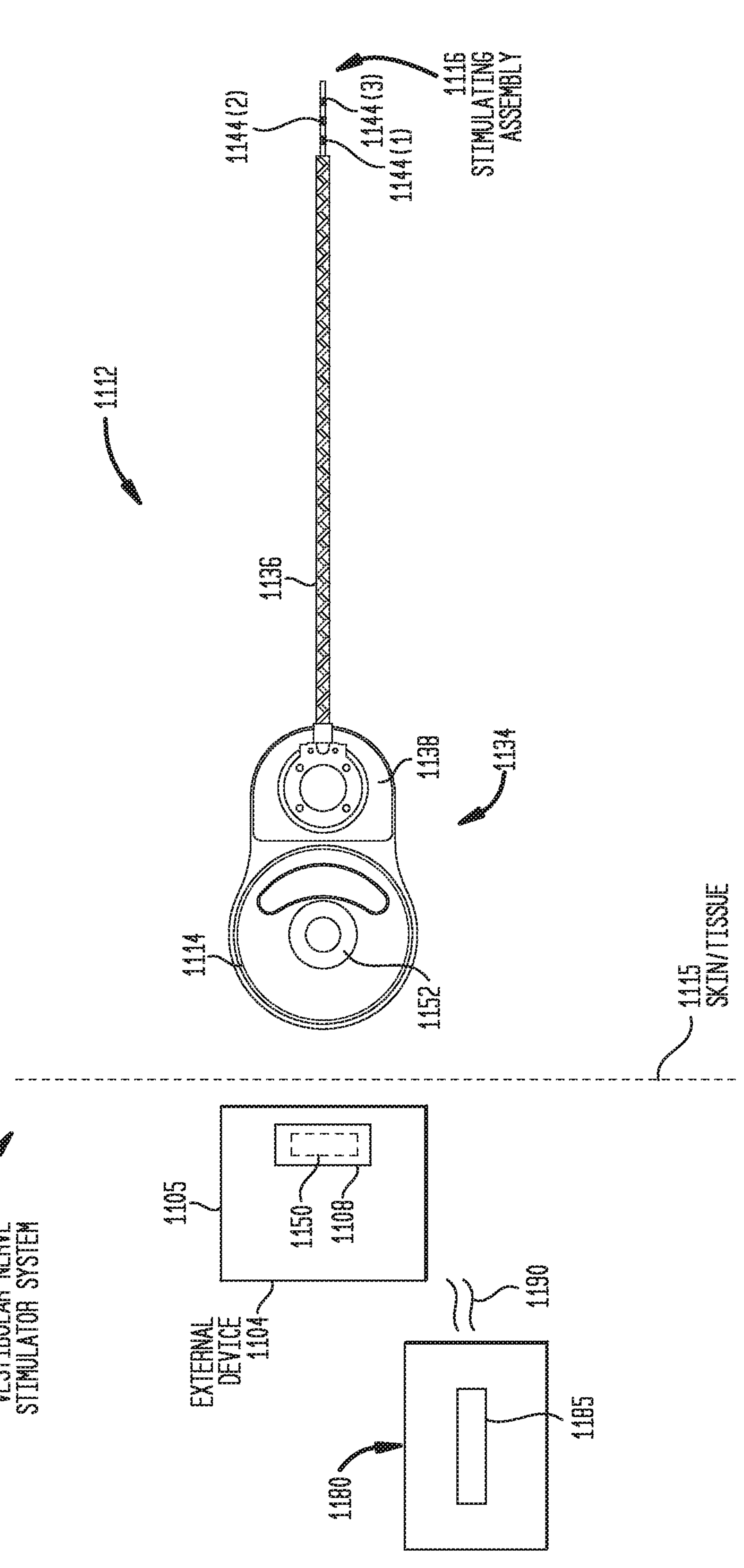
FIG. 11 is a schematic diagram illustrating a vestibular implant, in accordance with certain embodiments presented herein.

For example, FIG. 11 illustrates an example vestibular stimulator system 1102 in accordance with embodiments presented herein. In this example, the vestibular stimulator system 1102 comprises an implantable component (vestibular stimulator) 1112 and an external device/component 1104 (e.g., external processing device, battery charger, remote control, etc.).

The vestibular stimulator 1112 comprises an implant body (main module) 1134, a lead region 1136, and a stimulating assembly 1116, all configured to be implanted under a skin/tissue flap (skin flap) 1115 of the recipient. The implant body 1134 generally comprises a hermetically-sealed housing 1138 in which RF interface circuitry, one or more rechargeable batteries, one or more processors, and a stimulator unit are disposed. The implant body 134 also includes an internal/implantable coil 1114 that is generally external to the housing 1138, but which is connected to the transceiver via a hermetic feedthrough (not shown).

The stimulating assembly 1116 comprises a plurality of electrodes 1144 disposed in a carrier member (e.g., a flexible silicone body). In this specific example, the stimulating assembly 1116 comprises three (3) stimulation electrodes, referred to as stimulation electrodes 1144(1), 1144(2), and 1144(3). The stimulation electrodes 1144(1), 1144(2), and 1144(3) function as an electrical interface for delivery of electrical stimulation signals to the recipient's vestibular system.

The stimulating assembly 1116 is configured such that a surgeon can implant the stimulating assembly adjacent the recipient's otolith organs via, for example, the recipient's oval window. It is to be appreciated that this specific embodiment with three stimulation electrodes is merely illustrative and that the techniques presented herein may be used with stimulating assemblies having different numbers of stimulation electrodes, stimulating assemblies having different lengths, etc.

In accordance with embodiments presented herein, the external device 1104 can include an integrated external magnet 1150 configured to be magnetically coupled to an implantable magnet 1152 in the vestibular stimulator 1112. The external device 1104 also includes an integrated external coil 1108 that is configured to be wirelessly (e.g., inductively) coupled to the implantable coil 1114 of the vestibular stimulator 1112. In FIG. 11, the external magnet 1150 is shown using dashed lines, indicating the external coil 1108 disposed around the magnet 1150. The magnets 1150 and 1152 magnetically couple the external device 1104 to the vestibular stimulator 1112 through the skin flap 1115.

After the vestibular stimulator 1112 is placed within the recipient's head, the external device 1104 is attached to the head, with the external magnet 1150 magnetically coupling the external device 1104 to the implantable magnet 1152 of the vestibular stimulator 1112 through the skin flap 1115. While a strength of the implantable magnet 1152 generally is fixed and cannot readily be changed post-surgery, a strength of the external magnet 1150 may be customized for the recipient. For example, different external devices 1104 with different external magnets 1150 having different strengths may be selectively coupled and decoupled to the vestibular stimulator 1112 until the external device 1104 with the most suitable external magnet 1150 is chosen. Alternatively, the external magnet 1150 may be removably integrated within the housing 1105 of the external device 1104, and different external magnets 1150 having different strengths may be integrated and de-integrated within the housing 1105 until the most suitable external magnet 1150 is chosen.

The external magnet 1150 may be chosen to provide as comfortable of a fit as possible for the recipient while achieving an appropriate strength of attraction between the external magnet 1150 and the implantable magnet 1152. While a stronger external magnet 1150 may provide a stronger coupling with the implantable magnet 1152, e.g., making it less likely for the external magnet 1150 to fall off during use, the stronger external magnet 1150 could cause pain for the recipient, e.g., by pulling on the recipient's head or creating a rash on the recipient's skin. The strength of the external magnet 1150 may be selected to balance these concerns. For example, the external magnet 150 could be selected from magnets having strengths of about ½M (weakest), 1 M, 2 M, 3 M, 4 M, 5 M, or 6 M (strongest). As would be recognized by a person of ordinary skill in the art, this range of magnet strengths is illustrative and should not be construed as being limiting in any way.

In certain example embodiments, an implant configuration system 1180, which may be similar to implant configuration system 180 of FIGS. 1-4, is configured to determine and/or set the operational parameters of the vestibular stimulator 1112 based on the strength of the external magnet 1150. For example, the implant configuration system 1180 can include a memory and processor with logic 1185 configured to estimate the thickness of the skin flap 1115 based on the strength of the external magnet 1150 and to determine the operational parameters based on the estimated skin flap thickness (SFT). The implant configuration system 1180 can provide and/or display the determined operational parameters (e.g., to the recipient and/or a clinician aiding the recipient) and/or adjust one or more settings associated with the vestibular implant 1102 based on the determined operational parameters via one or more data links 1190, such as a wired connection, a wireless network, radio frequency, infrared, or another suitable wired or wireless communication mechanism or combinations thereof.

It is to be appreciated that the embodiments presented herein are not mutually exclusive and that the various embodiments may be combined with another in any of a number of different manners. The invention described and claimed herein is not to be limited in scope by the specific preferred embodiments herein disclosed, since these embodiments are intended as illustrations, and not limitations, of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

What is claimed is:

1. A method, comprising:

identifying a magnetization of a magnet of an external component of an implantable medical device system, the magnet being configured to magnetically couple the external component to an implantable component of the implantable medical device system by applying a magnetic field through a skin flap of a recipient of the implantable medical device system;

estimating a thickness of the skin flap based on the magnetization of the magnet;

determining at least one operational parameter of the implantable medical device system based on the estimated thickness of the skin flap; and setting the at least one operational parameter of the implantable medical device system.

2. The method of claim 1, wherein the at least one operational parameter affects a battery autonomy for the external component.

3. The method of claim 2, comprising determining a range of battery autonomy times for the external component.

4. The method of claim 1, wherein the at least one operational parameter is related to a suitability of a battery type for the external component.

5. The method of claim 1, wherein the at least one operational parameter is related to a signal attenuation associated with the implantable medical device system.

6. The method of claim 1, wherein estimating the thickness of the skin flap comprises calculating a range of skin flap thicknesses corresponding to the magnetization of the magnet.

7. The method of claim 1, wherein estimating the thickness of the skin flap comprises identifying a weighted distribution of skin flap thicknesses corresponding to the magnetization of the magnet.

8. The method of claim 1, further comprising displaying the at least one operational parameter on a display of a computing device.

9. The method of claim 1, further comprising displaying the estimated thickness of the skin flap on a display of a computing device.

10. The method of claim 1, wherein estimating the thickness of the skin flap based on the magnetization of the magnet comprises:

using data associating each of a plurality of thicknesses of the skin flap to a respective, corresponding magnetization; and selecting the thickness of the skin flap based on the data associating the thickness of the skin flap to the magnetization of the magnet of the external component.

11. The method of claim 10, wherein the data comprises at least one of a lookup table, a chart, or an algorithmic model.

12. The method of claim 1, wherein the at least one operational parameter of the implantable medical device system is associated with coil tuning, an auditory detection sound threshold, or a sound stimulation comfort level.

13. A method, comprising:

providing an external component of an implantable medical device system, wherein the external component comprises a magnet for magnetically coupling the external component to an implantable component by applying a magnetic field through a skin flap of a recipient of the implantable medical device system;

estimating a thickness of the skin flap based on a magnetization of the magnet; and setting one or more operational parameters of the implantable medical device system based on the estimated thickness of the skin flap.

14. The method of claim 13, wherein the one or more operational parameters are related to a battery autonomy for the external component.

15. The method of claim 13, wherein the one or more operational parameters are related to a suitability of a battery type for the external component.

16. The method of claim 13, wherein the one or more operational parameters are related to a signal attenuation associated with the implantable medical device system.

17. The method of claim 13, further comprising displaying the one or more operational parameters on a display of a computing device.

18. The method of claim 13, further comprising displaying the estimated thickness of the skin flap on a display of a computing device.

19. The method of claim 13, wherein estimating the thickness of the skin flap comprises calculating a range of skin flap thicknesses corresponding to the magnetization of the magnet.

20. The method of claim 13, wherein estimating the thickness of the skin flap comprises identifying a weighted distribution of skin flap thicknesses corresponding to the magnetization of the magnet.

21. One or more non-transitory computer readable storage media comprising instructions that, when executed by at least one processor, are operable to:

estimate, based on a magnetization of a magnet of an external component of an implantable medical device system, a thickness of a skin flap through which the magnet is configured to apply a magnetic field to magnetically couple the external component to an implantable component of the implantable medical device system; and cause at least one operational parameter of the implantable medical device system to be set based on the estimated thickness of the skin flap.

22. The one or more non-transitory computer readable storage media of claim 21, wherein the at least one operational parameter is related to a battery autonomy for the external component.

23. The one or more non-transitory computer readable storage media of claim 22, wherein the instructions, when executed by the at least one processor, are further operable to:

determine the at least one operational parameter by determining a range of battery autonomy times for the external component.

24. The one or more non-transitory computer readable storage media of claim 21, wherein the at least one operational parameter is related to a suitability of a battery type for the external component.

25. The one or more non-transitory computer readable storage media of claim 21, wherein the at least one operational parameter is related to a signal attenuation associated with the implantable medical device system.

26. The one or more non-transitory computer readable storage media of claim 21, wherein the instructions, when executed by the at least one processor, are further operable to:

estimate the thickness of the skin flap by calculating a range of skin flap thicknesses corresponding to the magnetization of the magnet.

27. The one or more non-transitory computer readable storage media of claim 21, wherein the instructions, when executed by the at least one processor, are further operable to:

estimate the thickness of the skin flap by identifying a weighted distribution of skin flap thicknesses corresponding to the magnetization of the magnet.

28. The one or more non-transitory computer readable storage media of claim 21, wherein the instructions, when executed by the at least one processor, are further operable to:

cause the at least one operational parameter to be displayed on a display of a computing device.

29. The one or more non-transitory computer readable storage media of claim 21, wherein the instructions, when executed by the at least one processor, are further operable to:

cause the estimated thickness of the skin flap to be displayed on a display of a computing device.

* * * * *